(12) United States Patent
Lin

(10) Patent No.: US 7,410,632 B2
(45) Date of Patent: *Aug. 12, 2008

(54) EXTRACTION PROCESS FOR REMOVAL OF IMPURITIES FROM MOTHER LIQUOR IN THE SYNTHESIS OF CARBOXYLIC ACID

(75) Inventor: Robert Lin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 461 days.

This patent is subject to a terminal disclaimer.

(21) Appl. No.: 10/455,016

(22) Filed: Jun. 5, 2003

(65) Prior Publication Data

US 2004/0244536 A1 Dec. 9, 2004

(51) Int. Cl.
C07C 51/43 (2006.01)
(52) U.S. Cl. .............................. 423/658.5; 423/DIG. 14; 562/416; 562/485; 562/487; 562/414; 562/412; 562/608
(58) Field of Classification Search .................... 423/49, 423/658.5, DIG. 14; 562/416, 485, 486, 562/487, 414, 409, 412, 608
See application file for complete search history.

(56) References Cited

U.S. PATENT DOCUMENTS

| | | | |
|---|---|---|---|
| 2,964,559 A | 12/1960 | Burney et al. | |
| 3,840,641 A | 10/1974 | Wampfier et al. | |
| 3,873,468 A | 3/1975 | Kobinata et al. | |
| 3,950,409 A | 4/1976 | Yokota et al. | |
| 3,996,271 A | 12/1976 | Yokota et al. | |
| 4,081,464 A | 3/1978 | Marsh et al. | |
| 4,158,738 A | 6/1979 | Scott et al. | |
| 4,185,073 A | 1/1980 | Marsh et al. | |
| 4,219,669 A | 8/1980 | Tsuchiya et al. | |
| 4,298,580 A | 11/1981 | Harper et al. | |
| 4,330,676 A | 5/1982 | Moxham | |
| 4,356,319 A | 10/1982 | Roffia et al. | |
| 4,769,489 A | 9/1988 | Abrams et al. | |
| 4,914,230 A | 4/1990 | Abrams et al. | |
| 4,939,297 A | 7/1990 | Browder et al. | |
| 5,200,557 A | 4/1993 | Gee et al. | |
| 5,643,468 A | 7/1997 | Ure | |
| 5,676,847 A | 10/1997 | Yamamoto et al. | |
| 5,705,682 A * | 1/1998 | Ohkoshi et al. ............. | 562/414 |
| 5,770,765 A | 6/1998 | Ohkashi | |
| 5,840,965 A | 11/1998 | Turner et al. | |
| 5,916,422 A | 6/1999 | Kimura et al. | |
| 5,955,394 A | 9/1999 | Kelly | |
| 6,054,610 A | 4/2000 | Lee et al. | |
| 6,133,476 A | 10/2000 | Lin | |
| 6,153,790 A | 11/2000 | June et al. | |
| 6,562,997 B2 | 5/2003 | Sikkenga et al. | |
| 7,074,954 B2 | 7/2006 | Sheppard et al. | |
| 7,132,566 B2 | 11/2006 | Sumner et al. | |
| 2001/0041811 A1 | 11/2001 | Sikkenga et al. | |
| 2002/0016500 A1 | 2/2002 | Matsumoto et al. | |
| 2002/0193630 A1 | 12/2002 | Lin et al. | |
| 2004/0225148 A1 | 11/2004 | Isogai et al. | |
| 2004/0245176 A1 | 12/2004 | Parker et al. | |
| 2007/0205153 A1 | 9/2007 | Parker et al. | |
| 2007/0208195 A1 | 9/2007 | Gibson et al. | |
| 2007/0208196 A1 | 9/2007 | Parker et al. | |
| 2007/0208197 A1 | 9/2007 | Gibson et al. | |
| 2007/0208198 A1 | 9/2007 | Parker et al. | |
| 2007/0208199 A1 | 9/2007 | Parker et al. | |
| 2007/0213557 A1 | 9/2007 | Seiki et al. | |

FOREIGN PATENT DOCUMENTS

| | | |
|---|---|---|
| DE | 2131470 A | 6/1970 |
| EP | 0 181 127 A2 | 5/1986 |
| EP | 0 764 627 A1 | 3/1997 |
| EP | 0579715 B1 | 8/1997 |
| EP | 1 484 305 A1 | 8/2004 |
| EP | 1 484 306 A1 | 8/2004 |
| GB | 892 766 | 3/1962 |
| GB | 1407705 | 9/1975 |

(Continued)

OTHER PUBLICATIONS

U.S. Appl. No. 10/455,018, Lin et al., filed Jun. 5, 2003.

(Continued)

*Primary Examiner*—Steven Bos
(74) *Attorney, Agent, or Firm*—Steven A. Owen; Bernard J. Graves, Jr.

(57) ABSTRACT

A method for removing impurities from a mother liquor comprising a carboxylic acid, a metal catalyst, impurities by (a) evaporating the mother liquor comprising a carboxylic acid, the metal catalyst, impurities, water and a solvent in a first evaporator zone to produce a vapor stream and a concentrated mother liquor stream; (b) evaporating the concentrated mother liquor stream in a second evaporator zone to form a solvent rich stream and a super concentrated mother liquor stream; (c) separating organic impurities with a water-solvent solution from the super concentrated mother liquor in a solid-liquid separation zone to form an aqueous stream and a second aqueous stream; (d) mixing in a mixing zone water and optionally and extraction solvent with the aqueous stream and second aqueous stream to form an aqueous mixture; and (e) adding an extraction solvent to the aqueous mixture in an extraction zone to form an extract stream and a raffinate stream.

16 Claims, 1 Drawing Sheet

FOREIGN PATENT DOCUMENTS

| | | |
|---|---|---|
| GB | 2067563 | 7/1981 |
| JP | 46-14339 B | 4/1971 |
| JP | 49-123191 A | 11/1974 |
| JP | 51-145488 A | 12/1976 |
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | WO 92/18453 | 10/1992 |
| WO | WO 92/18454 A1 | 10/1992 |
| WO | WO 93/24441 A | 12/1993 |
| WO | WO 97/27168 A1 | 7/1997 |
| WO | WO 93/30963 A | 8/1997 |
| WO | WO 00/31014 A1 | 6/2000 |
| WO | WO 01/55075 A2 | 8/2001 |

OTHER PUBLICATIONS

U.S. Appl. No. 10/455,017, Lin et al., filed Jun. 5, 2003.
BHS—Werk Sonthofen, *BHS-FEST Pressure Filter*, 1990, pamphlet, Santhofen, West Germany.
Copending U.S. Appl. No. 10/948,591, filed Sep. 24, 2004.
Copending U.S. Appl. No. 10/948,678, filed Sep. 24, 2004.
Copending U.S. Appl. No. 10/975,256, filed Oct. 28, 2004.
Copending U.S. Appl. No. 10/975,252, filed Oct. 28, 2004.
Office Action for copending U.S. Appl. No. 10/455,017.
USPTO office action dated Jan. 18, 2007 for copending U.S. Appl. No. 10/455,017.
USPTO office action dated Nov. 30, 2006 for copending U.S. Appl. No. 10/975,256.
USPTO office action dated Nov. 30, 2006 for copending U.S. Appl. No. 10/975,252.
USPTO office action dated Jul. 19, 2006 for copending U.S. Appl. No. 10/455,017.
USPTO office action dated Jul. 19, 2006 for copending U.S. Appl. No. 10/455,018.
Treybal, Robert E., "Stagewise Contact, Single-Stage Extraction," Mass-Transfer Operations, Third Edition, 1980, pp. 490-555, McGraw-Hill Book Company.
USPTO Office Action dated May 17, 2007 for copending U.S. Appl. No. 11/201,512.
Notice of Allowance dated Aug. 1, 2007 for copending U.S. Appl. No. 10/975,252.
Notice of Allowance dated Jul. 18, 2007 for copending U.S. Appl. No. 10/975,256.
Copending U.S. Appl. No. 11/839,575, filed Aug. 16, 2007, Philip Edward Gibson et al.
Copending U.S. Appl. No. 11/839,578, filed Aug. 16, 2007, Philip Edward Gibson et al.
Copending U.S. Appl. No. 11/839,582, filed Aug. 16, 2007, Philip Edward Gibson et al.
Copending U.S. Appl. No. 11/839,573, filed Aug. 16, 2007, Kenny Randolph Parker et al.
USPTO Office Action dated Oct. 16, 2007 for copending U.S. Appl. No. 11/655,317.
USPTO Office Action dated Sep. 25, 2007 for copending U.S. Appl. No. 11/655,396.
USPTO Office Action dated Sep. 25, 2007 for copending U.S. Appl. No. 11/655,395.
USPTO Office Action dated Sep. 11, 2007 for copending U.S. Appl. No. 10/455,017.
USPTO Notice of Allowance dated Sep. 11, 2007 for copending U.S. Appl. No. 10/455,018.
Copending U.S. Appl. No. 11/842,413, filed Aug. 21, 2007, Kenny Randolph Parker et al.
USPTO Office Action dated May 11, 2007 for copending U.S. Appl. No. 10/455,017.
USPTO Office Action dated May 14, 2007 for copending U.S. Appl. No. 10/455,018.
USPTO Notice of Allowance dated Dec. 3, 2007 for copending U.S. Appl. No. 10/455,017.
Copending U.S. Appl. No. 11/655,395, filed Jan. 19, 2007, Philip E. Gibson et al.
Copending U.S. Appl. No. 11/655,317, filed Jan. 19, 2007, Philip E. Gibson et al.
Copending U.S. Appl. No. 11/655,396, filed Jan. 19, 2007, Kenny R. Parker et al.

* cited by examiner

EXTRACTION PROCESS FOR REMOVAL OF IMPURITIES FROM MOTHER LIQUOR IN THE SYNTHESIS OF CARBOXYLIC ACID

FIELD OF INVENTION

This invention relates to the recovery of a metal catalyst from a mother liquor produced in the synthesis of carboxylic acid, typically terephthalic acid. More particularly, the process involves the addition of water to a super concentrated mother liquor stream to recover the metal catalyst and then subjecting an aqueous mixture so formed to a single stage extraction to remove organic impurities to produce an extract stream and a raffinate stream comprising the metal catalyst.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities present due to the oxidation of paraxylene.

Terephthalic acid (TPA) is an intermediate in the production of polyesters for plastics and fiber applications. Commercial processes for the manufacture of TPA are based on the heavy-metal catalyzed oxidation of p-xylene, generally with a bromide promoter in acetic acid solvent. Due to the limited solubility of TPA in acetic acid under practical oxidation conditions, a slurry of TPA crystals is formed in the oxidation reactor. Typically, the TPA crystals are withdrawn from the reactor and separated from the reaction mother liquor using conventional solid-liquid separation techniques. The mother liquor, which contains most of the catalyst and promoter used in the process, is recycled to the oxidation reactor. Aside from the catalyst and promoter, the mother liquor also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions in the oxidation of p-xylene to terephthalic acid.

The solid TPA crystals obtained by solid-liquid separation are generally washed with fresh solvent to displace the major portion of the mother liquor and then dried to remove most of the acetic acid solvent. The dried, crude TPA crystals are contaminated with impurities that were present in the mother liquor since these impurities are co-precipitated with the TPA crystals. Impurities are also present due to occlusion in the TPA crystal structure and due to incomplete removal of the mother liquor by the fresh solvent wash.

Many of the impurities in the mother liquor that are recycled are relatively inert to further oxidation. Such impurities include, for example, isophthalic acid, phthalic acid and trimellitic acid. Impurities, which undergo further oxidation are also present, such as, for example, 4-carboxybenzaldehyde, p-toluic acid and p-tolualdehyde. The concentration of oxidation inert impurities tends to accumulate in the mother liquor. The concentration of these inert impurities will increase in the mother liquor until an equilibrium is reached whereby the amount of each impurity contained in the dry TPA product balances its rate of formation or addition to the oxidation process. The normal level of impurities in crude TPA makes it unsuitable for direct use in most polymer applications.

Traditionally, crude TPA has been purified either by conversion to the corresponding dimethyl ester or by dissolution in water with subsequent hydrogenation over standard hydrogenation catalysts. More recently, secondary oxidative treatments have been used to produce polymer-grade TPA. Irrespective of the method used to purify TPA to render it suitable for use in polyester manufacture, it is desirable to minimize the concentrations of impurities in the mother liquor and thereby facilitate subsequent purification of TPA. In many cases, it is not possible to produce a purified, polymer-grade TPA unless some means for removing impurities from the mother liquor is utilized.

One technique for impurity removal from a recycle stream commonly used in the chemical processing industry is to draw out or "purge" some portion of the recycle stream. Typically, the purge stream is simply disposed of or, if economically justified, subjected to various treatments to remove undesired impurities while recovering valuable components. One example is U.S. # 4,939,297 herein incorporated by reference. The amount of purge required for control of impurities is process-dependent; however, a purge amount equal to 10-40% of the total mother liquor is usually sufficient for TPA manufacture. In the production of TPA, the level of mother liquor purge necessary to maintain acceptable impurity concentrations, coupled with the high economic value of the metal catalyst and solvent components of the mother liquor, make simple disposal of the purge stream economically unattractive. Thus, there is a need for a process that recovers essentially all of the expensive metal catalysts and acetic acid contained in the mother liquor while removing a major portion of the impurities present in the purge stream. The metal catalyst should be recovered in an active form suitable for reuse by recycling to the p-xylene oxidation step.

This invention is a marked improvement over a typical purge process. Some of the advantages are:
1) enhanced operability and reliability due to reduction in plugging potential;
2) reduction in overall energy usage.

The invention enhances the impurity removal efficacy of the process, and the operability of the process compared to the existing processes.

SUMMARY OF THE INVENTION

This invention relates to removal of impurities and the recovery of a metal catalyst from mother liquor produced in the synthesis of carboxylic acid, typically terephthalic acid. More particularly, the process involves the addition of water to a concentrated mother liquor to recover the metal catalyst and then subjecting an aqueous mixture so formed to a single stage extraction to remove organic impurities to produce an extract stream and a raffinate stream.

It is an object of this invention to provide a process to produce a super concentrated mother liquor stream.

It is yet another object of this invention to provide a process to recover a metal catalyst stream from a mother liquor stream.

It is yet another object of this invention to provide a process for removal of impurities and the recovery of a metal catalyst stream from mother liquor produced in the synthesis of carboxylic acid, In a first embodiment of this invention, a process to recover a metal catalyst from a mother liquor is provided. The process comprising the following steps:

(a) evaporating the mother liquor comprising a carboxylic acid, the metal catalyst, impurities, water and a solvent in a first evaporator zone to produce a vapor stream and a concentrated mother liquor stream;

(b) evaporating the concentrated mother liquor stream in a second evaporator zone to form a solvent rich stream and a super concentrated mother liquor stream;

(c) separating organic impurities with a water solvent solution from the super concentrated mother liquor in a solid-liquid separation zone to form an aqueous stream and a second aqueous stream;

(d) mixing in a mixing zone water and optionally and extraction solvent with the aqueous stream and the second aqueous stream to form an aqueous mixture;

(e) adding an extraction solvent to the aqueous mixture in an extraction zone to form an extract stream and a raffinate stream; and (f) optionally separating the extract stream in a separation zone to form a high boiling point organic impurities stream and a recovered extraction solvent stream.

In another embodiment of the invention, a process to produce a super concentrated mother liquor stream is provided. The process comprises the following steps:

(a) evaporating a mother liquor comprising a carboxylic acid, a metal catalyst, impurities, water and a solvent in a first evaporator zone to produce a vapor stream and a concentrated mother liquor stream; and (b) evaporating the concentrated mother liquor stream in a second evaporator zone to produce a solvent rich stream and a super concentrated mother liquor stream wherein the evaporating in step (a) and step (b) combined removes about 95 wt % to about 99 wt % of the solvent from the mother liquor; wherein second evaporator zone comprises an evaporator operated at a temperature of about 20° C. to about 70° C.

In another embodiment of the invention, a process to recover a metal catalyst from a mother liquor the process comprising the following steps:

(a) evaporating the mother liquor comprising a carboxylic acid, the metal catalyst, impurities, water and a solvent in a first evaporator zone to produce a vapor stream and a concentrated mother liquor stream;

(b) evaporating the concentrated mother liquor stream in a second evaporator zone to form a solvent rich stream and a super concentrated mother liquor stream; wherein about 85 wt % to about 99 wt % of the solvent and water is removed from the mother liquor in step (a) and step (b) combined;

(c) separating organic impurities with a water solution from the super concentrated mother in a solid-liquid separation zone to form an aqueous stream and a second aqueous stream; wherein a water-solvent solution is added to the solid liquid separation zone at a temperature range of about 20° C. to about 70° C.

(d) mixing in a mixing zone water and optionally and extraction solvent with the aqueous stream and the second aqueous stream to form an aqueous mixture;

(e) adding an extraction solvent to the aqueous mixture in an extraction zone to form an extract stream and a raffinate stream; and (f) optionally separating the extract stream in a separation zone to form a high boiling point organic impurities stream and a recovered extraction solvent stream.

These objects, and other objects, will become more apparent to others with ordinary skill in the art after reading this disclosure.

DESCRIPTION OF THE INVENTION

Figure 1:
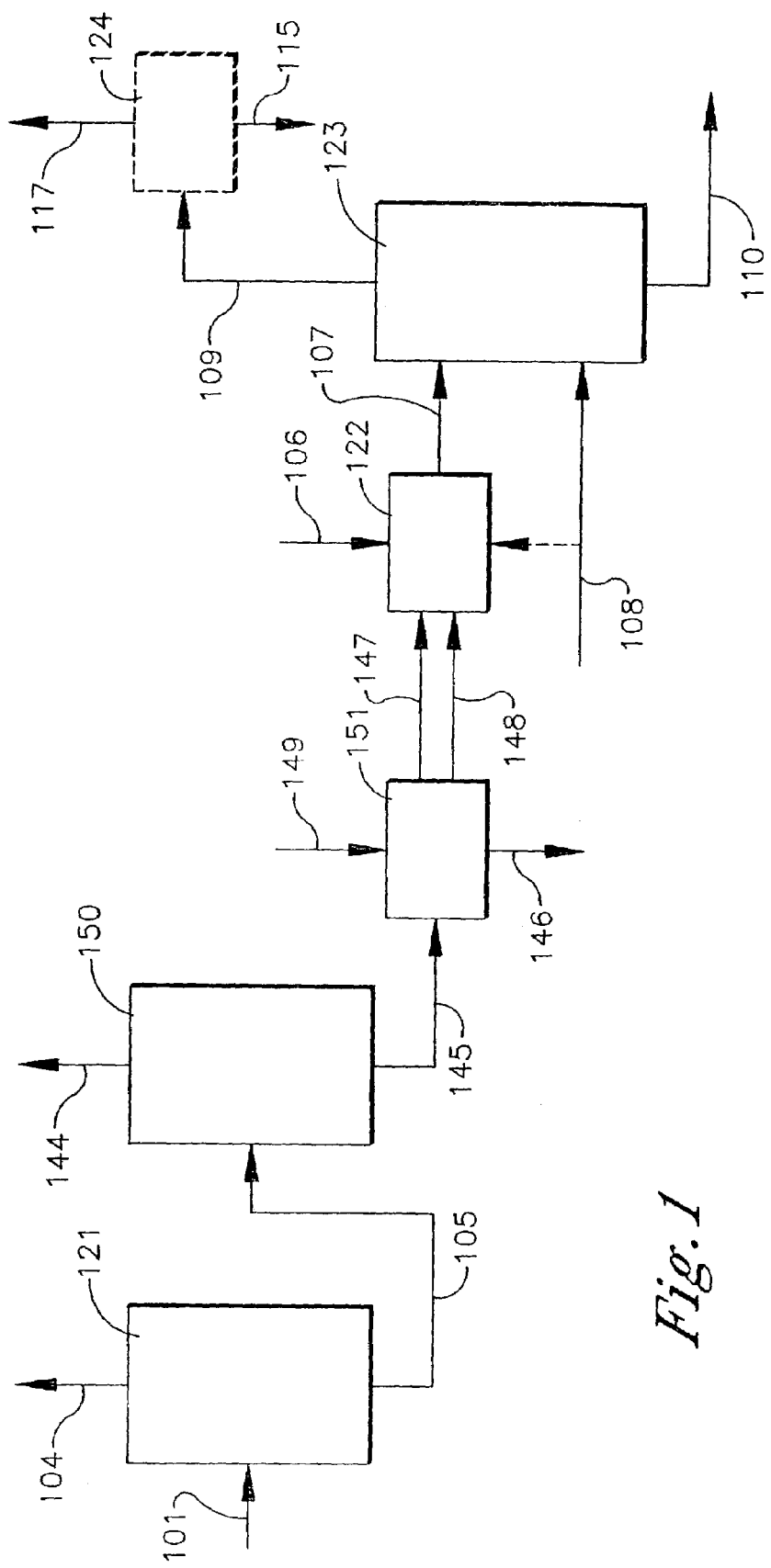
FIG. 1 illustrates different embodiments of the invention wherein a process to recover a metal catalyst from a mother liquor, a process to produce a super concentrated mother liquor stream is provided.

In one embodiment of this invention, a process to recover a metal catalyst from a mother liquor 101 is provided as shown in FIG. 1. The process comprises the following steps.

Step (a) comprises evaporating a mother liquor 101 comprising a carboxylic acid, the metal catalyst, impurities, water and a solvent in a first evaporator zone 121 to produce a vapor stream 104 and a concentrated mother liquor stream 105.

The mother liquor 101 is withdrawn from a carboxylic acid oxidative synthesis process. The mother liquor 101 serves as the feed stream to the present process. The mother liquor comprises carboxylic acid, water, a solvent, the metal catalyst and impurities. The impurities comprise organic bromides and corrosion metals. The organic bromides are used as promoters in the oxidation reaction. Examples of corrosion metals are iron and chromium compounds, which inhibit, reduce or entirely destroy the activity of the metal catalyst.

Suitable carboxylic acids are selected from the group consisting of terephthalic acid, isophthalic acid, naphthalene dicarboxylic acid, and mixtures thereof.

Suitable solvents include aliphatic mono-carboxylic acids, preferably containing 2 to 6 carbon atoms, or benzoic acid and mixtures thereof and mixtures with water. Preferably, the solvent is acetic acid mixed with water, in a ratio of about 5:1 to about 25:1, preferably between about 10:1 and about 15:1. Throughout the specification, acetic acid will be referred to as the solvent. However, it should be appreciated that other suitable solvents, such as those disclosed here, may also be utilized.

In the first step of the present process, the mother liquor is concentrated by conventional means in a first evaporator zone 121 comprising an evaporator to produce a vapor stream 104 and a concentrated mother liquor stream 105. The evaporator is operated at atmospheric or slightly superatmospheric conditions, generally from about 1 atmosphere to about 10 atmospheres. The vapor stream 104 comprises a majority of the water and solvent, and the concentrated mother liquor stream 105 comprises the remainder of the water and solvent not removed from the mother liquor 101. The evaporation removes about 50 wt % to about 80 wt % of the solvent and water, typically acetic acid and water, which are present in the mother liquor.

Step (b) comprises evaporating the concentrated mother liquor stream 105 in a second evaporator zone 150 to produce a solvent rich stream 144 and a super concentrated mother liquor stream 145.

The concentrated mother liquor stream 105 is then introduced in the second evaporator zone 150, which comprises at least one evaporator. The evaporator is operated at vacuum conditions. The evaporation is conducted at a temperature from about 20° C. to about 70° C.; another range is from about 30° C. to about 50° C. The combination of evaporators 121 and 150 are operated so as to concentrate the mother liquor as represented by stream 101 to a condition wherein about 75 to about 99 wt % of the solvent and water, typically acetic acid and water, is removed. Another range is the combination of evaporators 121 and 150 are operated so as to concentrate the mother liquor as represented by stream 101 to a condition wherein about 85 to about 99 wt % of the solvent and water, typically acetic acid and water, is removed. Further, ranges stated in this disclosure and the claims that follow should be understood to disclose the entire range specifically and not just the end point(s). For example, disclosure of the range 0 to 10 should be taken to specifically disclose 2, 2.5, 3.17 and all other number subsumed and not just 0 and 10.

Step (c) comprises separating organic impurities 146 with a water-solvent solution 149 from the super concentrated mother liquor stream 145 in a solid-liquid separation zone 151 to form an aqueous stream 147 and a second aqueous stream 148;

The solid-liquid separation step comprises feeding the super concentrated mother liquor stream 145 to a solid-liquid separation zone 151 to produce organic impurities 146, the aqueous stream 147 and the second aqueous stream 148. The solid-liquid separation zone 151 comprises at least one solid-liquid separation apparatus. There are no limitations on the type of solid-liquid separation apparatus employed. Examples of such apparatuses include, but are not limited to, filters, and centrifuges. The aqueous stream 145 is produced by the filtration of the super concentrated mother liquor stream 145.

The second aqueous stream 148 is produced by filtering of the super concentrated mother liquor stream 145, and washing with the water-solvent solution 149. The organic impurities 146 separated from the super concentrated mother liquor 145 in the solid-liquid separation zone 151 is subjected to extraction of metal oxidation catalyst by introduction of the water-solvent solution 149 to form the second aqueous stream 148 wherein at least 80% of the metal oxidation catalyst is recovered in the aqueous phases of the aqueous stream 147 and the second aqueous stream 148. Typically, at least 90% of the metal catalyst is recovered in the aqueous phases of the aqueous stream 147 and second aqueous stream 148. The aqueous stream 147 and the second aqueous stream 148 can optionally be combined before exiting the solid liquid separation zone 149.

The water-solvent solution 149 comprises water and optionally an additional solvent. The solvent can be any substance capable of dissolving the metal catalyst to form a uniformly dispersed solution at the molecular or ionic size level. Typically, the solvent comprises acetic acid, but solvents that have been previously mentioned in step (a) can also be utilized. Preferably, the extraction is performed in the same apparatus as the solid-liquid separation. Perhaps most surprisingly, is that by utilizing water as an extracting agent at temperatures in the range of about 20° C. to about 70° C., preferably about 30° C. to about 50° C., sufficient corrosion metal is retained in the organic impurities 146 wherein the need for corrosion metal removal by heating and filtering, as in other prior art methods, is eliminated. The organic purities 146 which represents solids stripped of metal catalyst can be disposed from the system.

Step (d) comprises mixing in a mixing zone 122 with water 106 and optionally an extraction solvent 108 an aqueous stream 147 and a second aqueous stream 148 to form an aqueous mixture 107;

The aqueous stream 147 and the second aqueous stream 148 can be combined the mixing zone 122. In one embodiment of the invention the mixing zone 122 comprises a conventional mixer. If necessary, the water-solvent solution 106 can be added to 122 in sufficient quantity to dissolve the metal catalyst in the aqueous mixture stream 107.

Generally, about 0.5-1.0 parts water per part of the aqueous stream 147 and second aqueous stream 148 combined are sufficient to dissolve the catalyst, preferably about 1:1 parts by weight. The addition of water not only recovers the metal catalyst, but also aids in pumping the resultant slurry to the extractor. It is desirable to keep the aqueous mixture 107 circulating with an external circulation loop. A small amount of extraction solvent 108, generally about 1 to about 10% by weight, preferably about 5% by weight may be added to the mixing zone 122 to enhance slurry handling by reducing adherence of solids to the side of vessels. This is represented by the dashed arrow from stream 108 in FIG. 1. It is desirable, but not necessary, to subject the aqueous mixture 107, prior to extraction, to a heat treatment at about 60° C. to about 95° C., another range is about 80° C. about 90° C. for about 0.5 to about 4 hours, preferably about 1 to about 2 hours. By this treatment, organic bromides are reacted to yield inorganic bromides which are preferentially retained in the aqueous fraction exiting the extractor. The quantity of bromine-containing compounds purged from the system along with the unwanted impurities is thereby minimized. The heat treatment conserves bromides and simplifies disposal of the organic impurities.

Step (e) comprises adding an extraction solvent 108 to the aqueous mixture 107 in an extraction zone 123 to form an extract stream 109 and the raffinate stream 110.

The aqueous mixture 307 or the purified aqueous mixture 308 is fed to an extraction zone 323 wherein the aqueous mixture 307 or the purified aqueous mixture 308 and the extraction solvent 311 are contacted in the extraction zone 323. The aqueous mixture 307 or the purified aqueous mixture 308 and the extraction solvent 311 are mixed to form an extract stream 309 comprising solvent, water organic impurities, and organic solvent which forms a lighter phase, and the raffinate stream 310 comprising a metal catalyst, corrosion metals, and water. The extract stream 309 is withdrawn as an overhead stream, and the raffinate stream 310 is withdrawn from the bottom of the extractor in the extraction zone 323. In this invention, one embodiment of the extraction zone 323 is a single stage extractor. In an embodiment of the invention, the extraction zone comprises a counter current extractor.

The extraction solvent 108 used in the extractor should be substantially water-insoluble to minimize the amount of organic solvent dissolved in the aqueous fraction. Additionally, the extraction solvent 108 is preferably an azeotropic agent which serves to assist solvent recovery from the organic extract. Solvents which have proven to be particularly useful are C1 to C6 alkyl acetates, particularly n-propyl acetate (n-PA), isopropyl acetate, isobutyl acetate, sec-butyl acetate, ethyl acetate and n-butyl acetate, although other water-insoluble organic solvents having an appropriate density and a sufficiently low boiling point may also be used, such as p-xylene. N-propyl acetate and isopropyl acetate are particularly preferred due to their relatively low water solubility, excellent azeotropic behavior, and their ability to remove the remaining acetic acid as well as high-boiling organic impurities from the aqueous mixture.

The extraction can be effected using solvent ratios from about 1-4 parts by weight solvent per part of extractor feed depending on the extractor feed composition. Space velocities of the combined feeds to the extractor generally range from 1 to about 3 $hr^{-1}$. Although the extraction can be done at ambient temperature and pressure, heating the solvent and extractor to about 30° C. to about 70° C., another range of about 40° C. to about 60° C. can be used. Although the extract stream 109 comprises small amounts of the metal catalyst and corrosion metals, essentially all of the metal catalyst and the majority of the remaining corrosion metals are contained in the heavier phase, raffinate stream 110.

Step (f) comprises optionally separating the extract stream 109 in a separation zone 124 to form a high boiling point organic impurities stream 115 and a recovered extraction solvent stream 117.

The extract stream 109 comprises organic solvent and organic impurities. The extract stream 109 can further comprises acetic acid and water, often in minor amounts. The extract stream 109 may be distilled in a separation zone comprising conventional distillation equipment. Convention distillation equipment includes, for example, a distillation column.

Most of the organic impurities are extracted by the organic solvent in the extraction zone, 123. This occurs because the organic impurities show a high degree of solubility for the organic solvent and to a lesser extent for acetic acid. By distilling the lighter phase from the extractor, the organic solvent is evaporated allowing the organic impurities to concentrate in the column underflow.

The recovered extraction solvent stream 117 may be recycled to the extractor in the extraction zone 123 and oxidative reactor, respectively. The high-boiling organic impurities stream 115 are removed as sludge from the base of the distillation column for disposal.

Although the composition of the various streams in the process varies depending on the process conditions, a typical composition of the streams are shown in Table 1. In Table 1, the components are shown in the left hand column and the amount of these components in each stream in the FIG. 1 are shown in the number column corresponding to the number of the stream in FIG. 1. The amounts of the components shown in Table 1 can be any measurement of weight as long as it is consistent for all components and all streams. For example, the mother liquor 301 has acetic acid in the amount of 915 pounds, 915 grams, etc.

I claim:
1. A process comprising the following steps:
   (a) evaporating a mother liquor comprising a carboxylic acid, a metal catalyst, impurities, water and a solvent in a first evaporator zone to produce a vapor stream and a concentrated mother liquor stream;
   (b) evaporating said concentrated mother liquor stream in a second evaporator zone to form a solvent rich stream and a super concentrated mother liquor stream;
   (c) separating organic impurities with a water-solvent solution from said super concentrated mother liquor stream in a solid-liquid separation zone to form an aqueous stream and a second aqueous stream;
   (d) mixing in a mixing zone water and optionally an extraction solvent with said aqueous stream and said second aqueous stream to form an aqueous mixture;
   (e) adding an extraction solvent to said aqueous mixture in an extraction zone to form an extract stream and a raffinate stream; and
   (f) optionally separating said extract stream in a separation zone to form a high boiling point organic impurities stream and a recovered extraction solvent stream.

2. The process according to claim 1 wherein about 50 wt % to about 80 wt % of said solvent and water is removed from said mother liquor in step (a).

3. The process according to claim 2 wherein about 75 wt % to about 99 wt % of said solvent and water is removed from said mother liquor in step (a) and step (b) combined.

4. The process according to claim 1 wherein about 85 wt % to about 99 wt % of said solvent and water is removed from said mother liquor in step (a) and step (b) combined.

5. The process according to claim 1 wherein about 90 wt % to about 99 wt % of said solvent and water is removed from said mother liquor in step (a) and step (b) combined.

TABLE 1

Material Balance
Process Material Balance
Stream in FIG. 1

| | 101 | 104 | 105 | 144 | 145 | 146 | 147 | 148 | 149 | 106 | 107 | 108 | 109 | 110 |
|---|---|---|---|---|---|---|---|---|---|---|---|---|---|---|
| Acetic Acid | 915.0 | 534.1 | 380.9 | 289.5 | 91.5 | 0.8 | 9.1 | 81.5 | — | — | 90.6 | — | 88.6 | 2.0 |
| Water | 55.0 | 39.3 | 15.7 | 13.1 | 2.6 | 0.7 | 0.3 | 7.8 | 6.2 | 80.0 | 88.1 | — | 57.2 | 30.9 |
| n-Propyl Acetate | — | — | — | — | — | — | — | — | — | — | — | 400.0 | 399.2 | 0.8 |
| Terephthalic Acid | 0.71 | — | 0.71 | — | 0.71 | 0.62 | 0.07 | 0.02 | — | — | 0.09 | — | 0.09 | — |
| Isophthalic Acid | 5.83 | — | 5.83 | — | 5.83 | 4.98 | 0.58 | 0.26 | — | — | 0.85 | — | 0.84 | — |
| Phthalic Acid | 3.81 | — | 3.81 | — | 3.81 | 0.03 | 0.38 | 3.39 | — | — | 3.78 | — | 3.60 | 0.18 |
| Benzoic Acid | 8.12 | 0.06 | 8.06 | 0.02 | 8.04 | 0.07 | 0.80 | 7.17 | — | — | 7.97 | — | 7.96 | — |
| 4-Carboxybenzaldehyde | 1.56 | — | 1.56 | — | 1.56 | 1.23 | 0.16 | 0.17 | — | — | 0.33 | — | 0.33 | — |
| Trimellitic Acid | 1.17 | — | 1.17 | — | 1.17 | 0.21 | 0.12 | 0.84 | — | — | 0.96 | — | 0.90 | 0.07 |
| Paratoluic Acid | 2.96 | 0.01 | 2.95 | — | 2.94 | 1.60 | 0.29 | 1.05 | — | — | 1.35 | — | 1.34 | 0.01 |
| Paratolualdehyde | 0.51 | 0.05 | 0.46 | 0.03 | 0.44 | — | 0.04 | 0.39 | — | — | 0.43 | — | 0.43 | — |
| Others | 2.50 | — | 2.50 | — | 2.50 | 0.45 | 2.05 | — | — | — | 2.05 | — | 2.03 | 0.02 |
| Organic Bromide | 1.30 | — | 1.30 | — | 1.30 | 0.07 | 1.24 | — | — | — | 0.37 | — | 0.37 | — |
| Ionic Bromide | 0.34 | — | 0.34 | — | 0.34 | 0.02 | 0.32 | — | — | — | 1.23 | — | 0.01 | 1.22 |
| Cobalt | 1.44 | — | 1.44 | — | 1.44 | 0.07 | 0.68 | 0.68 | — | — | 1.37 | — | 0.01 | 1.35 |
| Manganese | 0.10 | — | 0.10 | — | 0.10 | — | 0.05 | 0.05 | — | — | 0.10 | — | — | 0.09 |
| Corrosion Metals | 0.08 | — | 0.08 | — | 0.08 | 0.02 | 0.06 | — | — | — | 0.06 | — | — | 0.06 |
| Total | 1000 | 573 | 427 | 303 | 124 | 11 | 16 | 103 | 6 | 80 | 200 | 400 | 563 | 37 |

*The amounts of the components shown in Table 1 can be any measurement of weight as long as it is consistent for all components and all streams 6. The process according to claim 1 wherein said water-solvent solution is added to said solid liquid separation zone at a temperature range of about 20° C. to about 70° C.

7. The process according to claim 1 wherein said water-solvent solution is added to said solid liquid separation zone at a temperature range of about 30° C. to about 50° C.

8. The process according to claim 1 wherein said extraction zone comprises a counter current extractor.

9. The process according to claim 1 wherein said extraction zone comprises a single stage extractor.

10. The process according to claim 1 wherein said solvent rich stream comprises a solvent selected from the group consisting of n-propyl acetate, isopropyl acetate, isobutyl acetate, sec-butyl acetate, ethyl acetate and n-butyl acetate.

11. The process according to claim 1 wherein said second evaporator zone comprises an evaporator operated at a temperature of about 20° C. to about 70° C.

12. A process comprising the following steps:
 (a) evaporating a mother liquor comprising a carboxylic acid, a metal catalyst, impurities, water and a solvent in a first evaporator zone to produce a vapor stream and a concentrated mother liquor stream;
 (b) evaporating said concentrated mother liquor stream in a second evaporator zone to form a solvent rich stream and a super concentrated mother liquor stream; wherein about 85 wt % to about 99 wt % of said solvent and water is removed from said mother liquor in step (a) and step (b) combined;
 (c) separating organic impurities with a water-solvent solution from said super concentrated mother liquor stream in a solid-liquid separation zone to form an aqueous stream and a second aqueous stream; wherein said water-solvent solution is added to said solid liquid separation zone at a temperature range of about 20° C. to about 70° C.;
 (d) mixing in a mixing zone water and optionally an extraction solvent with said aqueous stream and said second aqueous stream to form an aqueous mixture;
 (e) adding an extraction solvent to said aqueous mixture in an extraction zone to form an extract stream and a raffinate stream; and
 (f) optionally separating said extract stream in a separation zone to form a high boiling point organic impurities stream and a recovered extraction solvent stream.

13. The process according to claim 12 wherein about 50 wt % to about 80 wt % of said solvent and water is removed from said mother liquor in step (a).

14. The process according to claim 12 wherein said extraction zone comprises a counter current extractor.

15. The process according to claim 12 wherein said extraction zone comprises a single stage extractor.

16. The process according to claim 12 wherein said solvent rich stream comprises a solvent selected from the group consisting of n-propyl acetate, isopropyl acetate, isobutyl acetate, sec-butyl acetate, ethyl acetate and n-butyl acetate.

* * * * *